United States Patent
Millot et al.

[11] Patent Number: 5,899,875
[45] Date of Patent: May 4, 1999

[54] DEVICE FOR PERCUTANEOUS ADMINISTRATION OF MEDICAMENTS FOR TREATING MALE IMPOTENCE

[75] Inventors: Philippe Millot, Dijon; Michel Lamoise, Bessey-les-Citeaux, both of France

[73] Assignee: Laboratoires D'Hygiene et de Dietetique (L.H.D.), Paris, France

[21] Appl. No.: 08/836,350
[22] PCT Filed: Nov. 16, 1995
[86] PCT No.: PCT/FR95/01510
§ 371 Date: May 12, 1997
§ 102(e) Date: May 12, 1997
[87] PCT Pub. No.: WO96/14897
PCT Pub. Date: May 23, 1996

[30] Foreign Application Priority Data

Nov. 16, 1994 [FR] France .................................. 94 13716

[51] Int. Cl.⁶ .............................. A61N 1/30; A61N 1/05; A61F 5/37
[52] U.S. Cl. .............................. 604/20; 607/143; 128/883
[58] Field of Search .............................. 604/20; 607/118, 607/143, 152, 153; 128/114.1, 883

[56] References Cited

U.S. PATENT DOCUMENTS

| | | |
|---|---|---|
| 926,384 | 6/1909 | Boyd . |
| 4,250,878 | 2/1981 | Jacobsen et al. ...................... 128/803 |
| 4,279,256 | 7/1981 | Bucalo ................................. 128/114.1 |
| 4,585,005 | 4/1986 | Lue et al. ............................. 128/114.1 |
| 5,192,271 | 3/1993 | Kalb et al. .............................. 604/116 |
| 5,282,468 | 2/1994 | Klepinski ................................ 607/118 |

FOREIGN PATENT DOCUMENTS

| | | |
|---|---|---|
| 86/07269 | 12/1986 | WIPO . |
| WO 86/07269 | 12/1986 | WIPO . |
| 94/15527 | 7/1994 | WIPO . |
| WO 94/15527 | 7/1994 | WIPO . |

*Primary Examiner*—Wynn Wood Coggins
*Assistant Examiner*—Sharon Finkel
*Attorney, Agent, or Firm*—Stevens, Davis, Miller & Mosher, L.L.P.

[57] ABSTRACT

A device for the percutaneous administration of a medicament for treating male impotence comprises two reservoirs (1,2) hydratable with a medicament solution and intended to be applied to the skin of the penis. The reservoirs are mounted on substantially cylindrical bracelet-shaped means (8) with an elastically expansible diameter to support and press the reservoirs (1,2) against said skin during the treatment. The device includes a sensor which is fixed on the bracelet and is sensitive to the expansion of the bracelet in order to deliver a signal to the user.

15 Claims, 1 Drawing Sheet

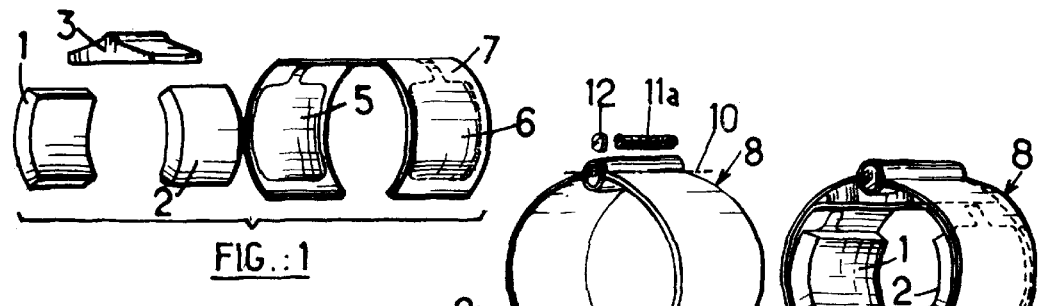
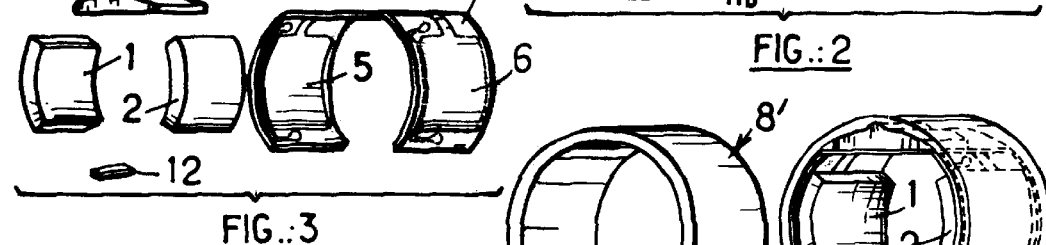
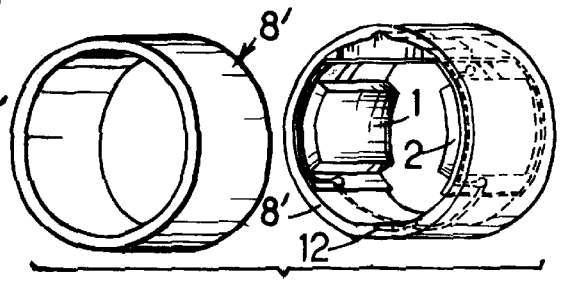
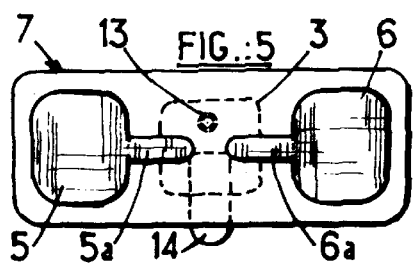
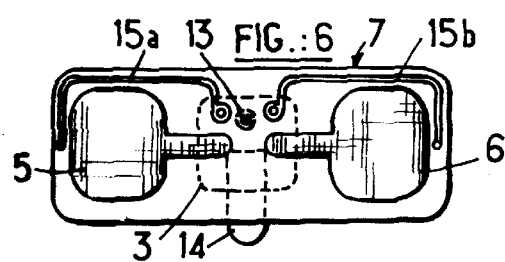
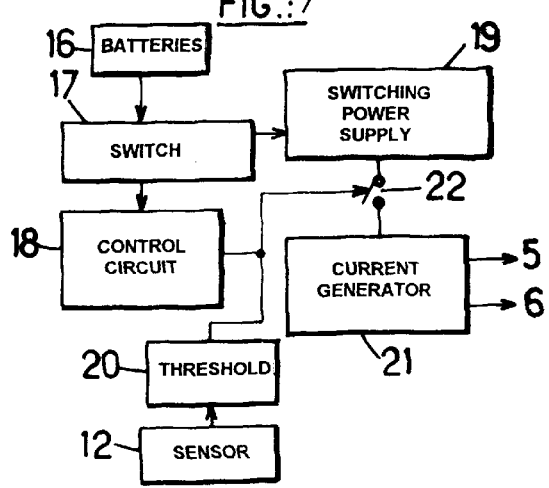
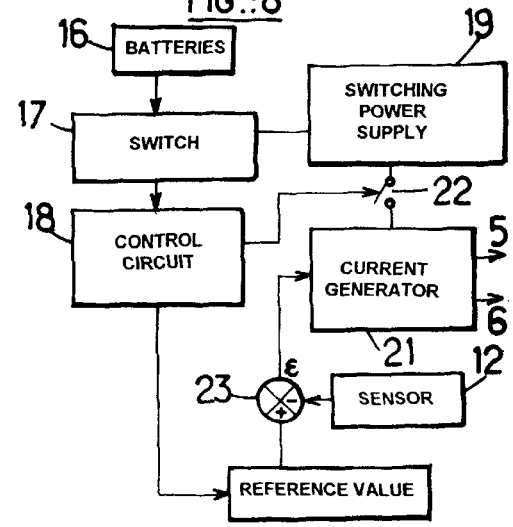

5,899,875

DEVICE FOR PERCUTANEOUS ADMINISTRATION OF MEDICAMENTS FOR TREATING MALE IMPOTENCE

FIELD OF THE INVENTION

The present invention relates to a device for percutaneous administration of a medicament for treating male impotence and, more particularly, to such a device comprising at least one reservoir which can be moisturized with a solution of the medicament and is designed to bear on the skin of the penis.

BACKGROUND OF THE INVENTION

Organic male impotence, that is to say erectile dysfunction, is in most cases of iatrogenic, hormonal, vascular or psychologic origin. Attempts have hitherto been made to treat this condition in some cases by injecting papaverine into the cavernous bodies of the penis. This technique presents various disadvantages. The administration of papaverine by injection is on the one hand painful and on the other hand dangerous. This is because it can result, in the long term, in irreversible lesions, such as the appearance of fibrous plates or nodules in the cavernous bodies. It sometimes also causes excessively prolonged erections, which have to be treated with other injections in order to reduce them. It has also been proposed to treat erectile dysfunction by purely mechanical means consisting of a pneumatic vacuum device which is fitted around the penis in order to provoke its erection. A ring then blocks any escape of blood from the cavernous bodies.

It is clear that these known treatment procedures are unsatisfactory on account of their traumatizing and/or dangerous nature and the pain which their use entails.

SUMMARY OF THE INVENTION

The present invention therefore has the aim of making available a device for treating male impotence which does not have any of these disadvantages and which thus ensures that this condition is treated in a manner which is painless, straightforward and without danger.

These aims of the invention, as well as others which will become apparent from reading the following description, are achieved by means of a device for percutaneous administration of a medicament for treating male impotence, comprising at least one reservoir which can be moisturized with a solution of the medicament and is designed to bear on the skin of the penis, this device being distinguished by the fact that it comprises a means in the form of a substantially cylindrical bracelet, of elastically expansible diameter, for supporting and pressing the moisturized reservoir against said skin throughout the duration of the treatment.

The expansible nature of the bracelet prevents the gradual swelling of the cavernous bodies during treatment from causing constriction of the penis by the bracelet, and a firm and continuous contact of the reservoir on the penis is afforded, which contact is necessary for the percutaneous administration of the medicament.

The device advantageously also comprises means, likewise supported by the bracelet, for assisting the passage of the medicament through the patient's skin by electrophoresis or ionophoresis. It is thus possible to control and monitor the flow of medicament passing through said skin. This control and monitoring can be refined, according to the invention, with the aid of a sensor which is fixed on the bracelet and is sensitive to the expansion of the latter in order to deliver a signal, representative of this expansion, to the means of assistance, in such a way as to ensure that these means are controlled as a function of the expansion of the bracelet, and thereby of the penis, under the effect of the swelling of the cavernous bodies.

It will be appreciated that by virtue of this sensor it is possible to stop the administration of the medicament in practice as soon as a sufficient erection has been obtained, which prevents any dangerous excess administration. It is also possible to control the administration of the medicament in accordance with a predetermined time program, as is traditional in the percutaneous administration of medication assisted by electrophoresis or ionophoresis.

According to one particular embodiment of the invention, the sensor consists of a strain gauge which is fixed on the bracelet so as to be sensitive to the expansion thereof.

BRIEF DESCRIPTION OF THE DRAWINGS

Other characteristics and advantages of the device according to the present invention will become apparent from reading the description which follows and from examining the attached drawing, in which:

FIG. 1 is an exploded view of a first embodiment of the device according to the invention, and FIG. 2 is a diagrammatic representation of this embodiment after its component parts have been assembled, FIG. 3 is an exploded view of a second embodiment of the device according to the invention, and FIG. 4 is a diagrammatic representation of this embodiment after its component parts have been assembled, FIGS. 5 and 6 are diagrammatic views showing the electrodes of the devices in FIGS. 2 and 4, respectively, developed in one plane, and FIGS. 7 and 8 are flow charts of two embodiments of means which are used for delivering an electric current for electrophoretic or ionophoretic assistance of administration of the medicament, which means can be used in the devices in FIGS. 2 and 4.

DETAILED DESCRIPTION OF THE INVENTION

Reference is made to FIG. 1 of the attached drawing which shows, in an exploded view, a diagrammatic representation of a first embodiment of the device according to the invention. Said device essentially comprises, by way of example, at least one reservoir 1 for a medicament, the active principle of which is a molecule capable of combating male impotence. Some examples of the molecules or classes of molecules which can be used in this application are moxisylyte and its salts, the agonist of vasoactive intestinal polypeptide, papaverine, alone or in combination with phentolamine, the agonist of prostaglandin E1, prostaglandin E1, the agonist of the beta-2 adrenergic receptor, the antagonist of 2-hydroxytryptamine, the antagonist of the alpha-2 adrenergic receptor, the agonist of dopa d2, the hydroxytryptamine re-uptake inhibitor, phenoxybenzamine, acetylcholine, sydnonimine and derivatives, testosterone, peripheral vasodilators, minoxidil and its derivatives, alprostadil and histamine H2 and H3 receptor agonists, such as impromidine.

The reservoir 1 can consist conventionally of a layer of a hydrated hydrogel with a solution of an active principle consisting of one of the abovementioned molecules, for example, just before the device is put in place. The reservoir 1 could also consist of a spongy or nonwoven product, impregnated with said solution. The device can advantageously comprise a second reservoir 2 made up like the first one. The two reservoirs are configured and dimensioned to bear on the skin of the penis during treatment. The device further comprises an electronic module 3, incorporating a source of electrical energy consisting of one or more batteries and means fed from this source for establishing and controlling a current passing from one reservoir to another, under the skin of the penis, in order to assist, by ionophoresis, the passage of an ionized form of the molecule of the active principle under said skin. By choosing the direction of the current, the administration of the active principle is performed selectively from one or other of the two reservoirs.

The device could of course comprise a single reservoir, the current then passing under the patient's skin between this reservoir and an adjacent "return" electrode pressed flat against the patient's skin.

To bring the reservoirs 1, 2 of the device in FIG. 1 into electrical contact with the source of the assist current, the reservoirs are pressed flat against two electrodes 5, 6, respectively, which are, for example, in the form of conductive layers deposited on a flexible film 7 by any known means. The film 7, on which the module 3 and the reservoirs 1 and 2 are attached and fixed in position, is itself fixed, in accordance with the present invention, in a bracelet 8, against the inner face of this bracelet, in accordance with the final assembly represented in FIG. 2. It will be seen that the bracelet 8 is made up of two rigid or semi-rigid parts 9a, 9b in the form of cylindrical shells which are articulated on each other about an axis 10. The two shells are stressed toward each other either by a helical spring 11a suitably arranged on the axis 10, or by an elastic strip 11b connecting those ends of the shells 9a, 9b which are not articulated on each other.

Of course, if one dispenses entirely with the assistance of ionophoresis, the device according to the invention can be reduced to the bracelet 8 and to one or more reservoirs such as 1 and 2.

It will be appreciated that by manually spreading the two shells open, it is possible to engage the device on the penis, as far as the root of the latter. In this position, after the shells have been released, the elastic means used (11a or 11b) press the reservoir or reservoirs 1 and 2 flat against the skin of the penis, with a slight elastic stress which is nevertheless sufficient to ensure that the device is maintained in this position without constriction of the penis, in accordance with one of the main aims of the present invention.

It then suffices to activate the electronic module 3 by operating a switch (not shown) so that an electric current passes between the electrodes 5 and 6, the module controlling the strength of the current in order to effect traditional administration of the medicament stored in one of the reservoirs.

According to the invention, the device can then advantageously comprise a sensor 12 mounted, for example, at the articulation of the two shells 9a, 9b so as to be sensitive to the mutual spreading-open of these shells. As this depends on the swelling of the cavernous bodies of the penis, it provides a measurement of this swelling, a measurement which is taken into account by the electronic module for the purpose of regulating or stopping the flow of medicament through the skin, as will be seen hereinafter in connection with FIGS. 7 and 8.

The sensor used for this purpose can consist of an extensometer gauge, for example the 02 UW-type gauge marketed by the United States company VISHAY, which gauge has very small dimensions (3 mm×5 mm). A sensor which is sensitive to a pressure or to a rotation (for example, a rotary potentiometer) of one shell with respect to the other could also be used.

FIG. 5 shows the film 7 developed in one plane. The electrodes 5 and 6 are formed on one face of the film and are electrically connected to the electronic module 3, fixed on the other face, via connections 5a, 6a respectively, formed on and through the film at the same time as the electrodes. The sensor 12 is likewise connected to the electronic module via connections which are not shown in FIG. 5. This figure shows an indicator element 13, such as a display diode mounted on the module 3 for the purpose of indicating to the user that the device is activated and that an assist current is passing between the two electrodes.

After fitting the device on the root of the penis, the user activates the device by operating a switch which can take various forms. In FIG. 5, said switch takes the form of a pull tab 14 which, in position, opens an electrical feed circuit of the module. By pulling the tab 14 of the device, the user closes the feed circuit and the module 3 produces the ionophoretic assist current which has to pass between the electrodes 5 and 6. When such an assist current is used, the reservoirs 1 and 2 must of course be impregnated with a solution of an ionized form of the abovementioned molecules of active principle.

Other types of switches could be used, of the slide type, or push type, optionally equipped with break points so that they can only be switched once. Reusing the device is then impossible, which may be desirable for reasons of hygiene and/or for pharmacological reasons.

The switch could further comprise a pull tab, like the pull tab 14, arranged to retract automatically when the device is positioned on the penis, for example due to the spreading-open of the shells of the device in FIG. 1, which takes place during this positioning.

It will be noted that the device according to the invention could advantageously be combined with a condom which is integral with the device or sold with it, in the same package.

Reference is now made to FIGS. 3 and 4 of the attached drawing which represent a second embodiment of the device according to the invention, which embodiment is distinguished from the previous embodiment essentially in terms of the form of the support bracelet and of the material used to make this bracelet. In FIGS. 3 and 4, reference numbers identical to reference numbers already used in FIGS. 1 and 2 designate identical or similar components or elements. In the exploded view in FIG. 3, it will be seen that the support bracelet has a cylindrical shape and internally supports the film 7, on which reservoirs 1, 2 and the electronic module 3 are fixed, as in the previous embodiment. The bracelet 8' is made of an extensible flexible material, knitted, woven or nonwoven. In the case of a knitted material, a jersey-type knit, highly extensible in one direction, is preferred. In the case of a nonwoven material, use will preferably be made of materials consisting of intrinsically elastic fibers, of the "Lycra" type (trademark), or other type. Preferred materials are those sold under the trade names Urgoband and Surgifix filed by the Applicant and by the company ADIFARM, respectively.

The various elements can be fixed on the bracelet 8', in the assembly represented in FIG. 4, by adhesive bonding or with fastening devices of the "Velcro" type (trademark) if, for example, it is desired to reuse the electronic module 3. With the bracelet in the embodiment in FIGS. 3 and 4, the sensor 12 used will preferably be an extensometer gauge adhesively bonded on the bracelet in that part thereof which is free of any other component, as represented in FIG. 4. The gauge is then electrically connected to the electronic module via conductors 15a, 15b configured as represented in FIG. 6, otherwise analogous to FIG. 5, the conductors 15a, 15b being formed on the film 7 at the same time as the electrodes 5, 6.

Reference is now made to FIG. 7 of the attached drawing in order to describe a first embodiment of the means for ionophoretic assistance which deliver an electrical current to the electrodes 5, 6. With the exception of the sensor 12, all the means represented in FIG. 7 are incorporated in the electronic module 3. The latter thus comprises, in addition to the batteries 16 and the starting switch 17 already mentioned, a control circuit 18, a switching power supply 19, an electronic threshold device 20, and a current generator 21. Closure of the switch 17 activates the control circuit 18 and the switching power supply 19. The latter allows the current generator 21, for example of the Howland type, to be fed with a voltage of several tens of volts, starting from the several volts output by the batteries 16. The supply to the generator 21 is controlled by the circuit 18 by way of an electronic switch 22, the circuit 18 being duly programmed to determine the strength and the wave form of the current output by the generator 21, as is known in the art. Thus, the output current is typically between 0 and 5 mA, either direct or alternating.

When, during treatment, the threshold device 20 receives from the sensor 12 a signal representative of a sufficient swelling of the penis, that is to say a signal exceeding a predetermined threshold, the device 18 controls the opening of the switch 22. The supply of an assist current to the device according to the invention is thus interrupted, which results in a great decrease in, or even discontinuation of, the flow of active principle responsible for said swelling. This arrangement eliminates any risk of needless or dangerous excess administration of the medicament. Means for regulating the threshold level can of course be incorporated in the device 20.

FIG. 8 shows a second embodiment of the means of ionophoretic assistance which can be incorporated in the device according to the invention. The components 16, 17, 18, 19 and 21 of the embodiment in FIG. 7 appear once again in FIG. 8. This embodiment is distinguished from the latter by the fact that it comprises means which permit time-programming of the administration of the medicament, as is known in the art. The control 18 in this case comprises means, optionally programmable, for calculating a reference value varying with time. This reference variable is compared at 23 with the signal delivered by the sensor, and the error signal $\in$ ensures regulation of the current supplied to the electrodes of the device by the current generator 21.

It is now clear that the device according to the invention easily achieves the objectives which were set, that is to say making available a form of treatment of male impotence which is convenient, painless and without any danger.

Of course, the invention is not limited to the embodiments which have been described and represented, as these have been given solely by way of example. Thus, certain parts of the device could be disposable (the electrodes and the reservoirs, for example), and others could be reusable (the electronic module 3, for example). Likewise, the printed circuit on which the constituent parts of the electronic module are fixed can be formed directly on one face of the film 7, the latter bearing the electrodes 5 and 6 on its other face. The circuit supports available on the market under the trademarks Kapton or Bendflex, for example, can then serve to constitute the film 7.

We claim:

1. A device for percutaneous administration of a medicament for treating male impotence, comprising at least one reservoir which can be moisturized with a solution of the medicament and is designed to bear on the skin of the penis, said device comprising a substantially cylindrical bracelet having an elastically expansible diameter, for supporting and pressing the moisturized reservoir against said skin throughout the duration of the treatment, assistance means supported by the bracelet for assisting the passage of the medicament through the patient's skin by ionophoresis, a sensor which is fixed on the bracelet and is sensitive to the expansion of the bracelet in order to deliver a signal, representative of this expansion, to the assistance means to ensure that the assistance means are controlled as a function of the expansion of the bracelet.

2. The device as claimed in claim 1, comprising means for turning off the assistance means when the signal received from the sensor exceeds a predetermined threshold.

3. The device as claimed in claim 1, wherein the assistance means comprise means for regulating an electrical assist current, the sensor forming part of the regulating means to ensure the monitoring of a reference variable by the assist current.

4. The device as in claim 1, wherein the sensor comprises a strain gauge which is fixed on the bracelet to be sensitive to the expansion thereof.

5. The device as claimed in claim 1, wherein the sensor consists of a strain gauge which is fixed on the bracelet so as to be sensitive to the expansion thereof.

6. The device as claimed in claim 1, wherein the bracelet comprises two inwardly curving, rigid parts which are articulated on one another about an axis defining a generatrix of the cylindrical surface of the bracelet, elastic means mounted on this axis stressing the two parts toward one another in the direction of closure of the bracelet.

7. The device as claimed in claim 1, wherein said bracelet is made of an elastically deformable material.

8. The device as claimed in claim 1, comprising a source of electrical energy supplying the assistance means for assisting the passage of the medicament into the body by ionophoresis, and an electrical switch operated by the user of the device in order to activate said assistance means.

9. The device as claimed in claim 8, wherein the switch is designed to be operated only once.

10. The device as claimed in claim 8, wherein the assistance means comprises at least first and second electrodes in direct or electrical contact with the reservoir and the patient's skin, respectively, and an electronic module supplied by the source of electrical energy so as to pass a current between the two electrodes.

11. The device as claimed in claim 10, wherein the electronic module comprises a switching power supply for increasing the voltage delivered by the source of electrical energy, and a current generator supplied with the voltage supplied by the switching power supply in order to pass a current between the two electrodes.

12. The device as claimed in claim 10, comprising a flexible film bearing the two electrodes on one face and the electronic module on the other face, the constituent parts of said module being implanted on a circuit printed directly on this face.

13. The device as claimed in claim 8, comprising an indicator which emits a light signal when the assistance means is activated.

14. The device as claimed in claim 1, wherein the active principle of the administered medicament is selected from the group consisting of: moxisylyte and its salts, the agonist of vasoactive intestinal polypeptide, papaverine, phentolamine, the agonist of prostaglandin E1, prostaglandin E1, the agonist of the beta-2 adrenergic receptor, the antagonist of 2-hydroxytryptamine, the antagonist of the alpha-2 adrenergic receptor, the agonist of dopa d2, the hydroxytryptamine re-uptake inhibitor, phenoxybenzamine, acetylcholine, sydnonimine and derivatives, testosterone, peripheral vasodilators, minoxidil and its derivatives, alprostadil, and histamine H2 and H3 receptor agonists.

15. The device as claimed in claim 1, combined with a condom.

* * * * *